(12) United States Patent
Yamanaka et al.

(10) Patent No.: US 6,387,918 B1
(45) Date of Patent: *May 14, 2002

(54) PHARMACEUTICAL COMPOSITION

(75) Inventors: Masayuki Yamanaka, Amagasaki; Fumio Shimojo, Kawanishi; Satoshi Ueda, Kawanishi; Toshihiko Toyoda, Kawanishi; Rinta Ibuki; Norio Ohnishi, both of Kyoto, all of (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,698
(22) PCT Filed: Feb. 18, 1998
(86) PCT No.: PCT/JP98/00665
  § 371 Date: Aug. 20, 1999
  § 102(e) Date: Aug. 20, 1999
(87) PCT Pub. No.: WO98/36747
  PCT Pub. Date: Aug. 27, 1998

(30) Foreign Application Priority Data

Feb. 20, 1997 (JP) .............................................. 9-036172
Sep. 22, 1997 (JP) .............................................. 9-256357

(51) Int. Cl.[7] .......................... A61K 31/44; A61K 31/55
(52) U.S. Cl. ....................................... 514/291; 514/214
(58) Field of Search ................................. 514/291, 214

(56) References Cited

U.S. PATENT DOCUMENTS 5,368,865 A * 11/1994 Asakura et al. ............. 424/498
5,385,907 A *  1/1995 Asakura et al. ............. 514/291
5,939,427 A *  8/1999 Kagayama et al. ......... 514/291

FOREIGN PATENT DOCUMENTS

EP    0 474 126 A   3/1992
EP    0 753 297 A   1/1997
WO    WO 96 13249 A  5/1996

OTHER PUBLICATIONS

Chemical Abstracts, vol. 122, No. 12, Mar. 20, 1995, Columbus, Ohio, US; abstract No. 142531, XP002070103, see abstract & JP 06 183 970 A (Fujisawa) Jul. 5, 1994.

* cited by examiner

Primary Examiner—Theodore J. Criares
Assistant Examiner—Jennifer Kim
(74) Attorney, Agent, or Firm—Oblon, Spivak, McClelland, Maier & Neustadt, P.C.

(57) ABSTRACT

A pharmaceutical composition comprising a tricyclic compound (I) or its pharmaceutically acceptable salt, an oil substance, a surfactant, a hydrophilic substance, water, and optionally a pH control agent, with enhanced stability, absorbability and/or a low irritation potential, is provided.

10 Claims, No Drawings

PHARMACEUTICAL COMPOSITION

TECHNICAL FIELD

This invention relates to a pharmaceutical composition comprising a tricyclic compound of general formula (I) or a pharmaceutically acceptable salt thereof which features stability, excellent absorbability, and/or a reduced irritation potential. This pharmaceutical composition is of value for the treatment or prevention of inflammatory or hyperproliferative skin diseases or cutaneous manifestations of immunologically-mediated diseases.

BACKGROUND ART

The tricyclic compound (I) and its pharmaceutically acceptable salt for use in accordance with this invention is known to have excellent immunosuppressive activity, antimicrobial activity and other pharmacological activities and, as such, be of value for the treatment or prevention of rejection reactions by transplantation of organs or tissues, graft-vs.-host diseases, autoimmune diseases, and infectious diseases [Japanese Kokai Tokkyo Koho S61-1481B1, EP-A-0323042, etc.].

Particularly, those species of tricyclic compound (I) which are designated as FR900506 (=FK506 Substance), FR900520, FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Oct. 5, 1984, accession number FERM BP-927] or *Streptomyces hygroscopicus* subsp. *vakushimaensis* No. 7238 [deposited with National Institute off Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Jan. 12, 1985, accession number FERM BP-928]. The FK506 Substance of the following chemical formula, in particular, is a representative compound.

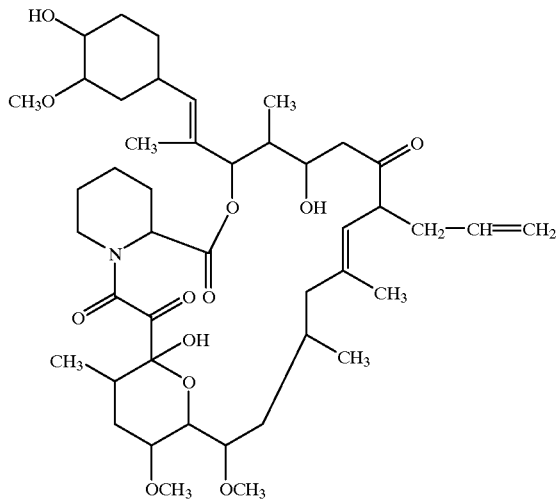

Chemical name: 17-allyl-1,14-dihydroxy-12-[2-(4-hydroxy-3-methoxycyclohexyl)-1-methylvinyl]-23, 25-dimethoxy-13,19,21,27-tetramethyl-11,28-dioxa-4-azatricyclo[22.3.1.0$^{4,9}$] octacos-18-ene-2,3,10, 16-tetraone It has been demonstrated that the above-mentioned FK506 Substance has quite excellent immunosuppressive activity and is useful for the treatment or prevention of rejection by organ transplantation and the treatment or prevention of diseases in the field of ophthalmology.

Japanese Kokai Tokkyo Koho H1-157913 discloses that a solution of FK506 Substance in ethanol is effective in the suppression of inflammation and that FK506 Substance can be formulated into a lotion, gel, or cream. However no specific dosage forms of the kinds are described.

Japanese Kokai Tokkyo Koho H5-17481 discloses an ointment comprising a tricyclic compound (I) or its pharmaceutically acceptable salt, at least a sufficient amount of a dissolution/absorption promoter to dissolve the same, and an ointment base.

W094/28894 discloses a lotion comprising a tricyclic compound (I) or its pharmaceutically acceptable salt, a dissolution/absorption promoter, a liquid medium, and optionally an emulsifier and/or a thickening (rheology modifier).

Heretofore, ointments have mainly been used in the treatment of skin diseases. However, different dosage forms suited to different clinical manifestations and different application sites are being demanded.

The inventors of this invention have studied possible pharmaceutical compositions for compounds of general formula (I) inclusive of FK506 Substance and found a dosage form having many desirable characteristics such as high stability, high transdermal absorbability, and/or reduced dermal irritancy. Thus, specifically this invention is directed to an hydrophilic semi-solid composition for external use containing said tricyclic compound.

DISCLOSURE OF INVENTION

In accordance with this invention there is provided a pharmaceutical composition comprising a tricyclic compound (I) or its pharmaceutically acceptable salt, an oil substance, a surfactant, a hydrophilic substance, and water, and further optionally a pH control agent.

The tricyclic compound for use in this invention can be expressed by the following general formula (I).

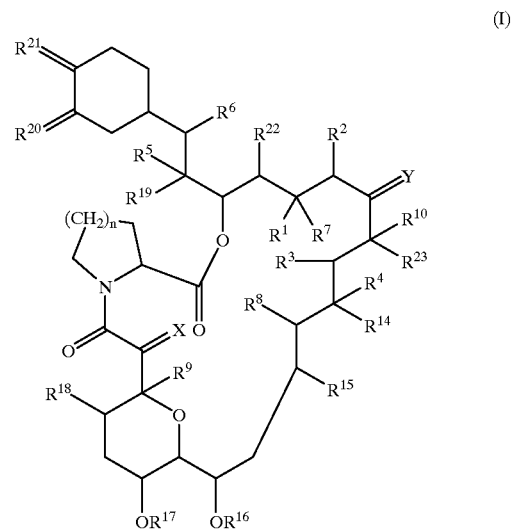

(wherein each of adjacent pairs of $R^1$ and $R^2$, $R^3$ and $R^4$ or $R^5$ and $R^6$ independently (a) is two adjacent hydrogen atoms, or (b) may form another bond formed between the carbon atoms to which they are attached, and further, $R^2$ may be an alkyl group;

$R^7$ is a hydrogen atom, a hydroxy group, a protected hydroxy group or an alkoxy group, or an oxo group together with $R^1$;

each of $R^8$ and $R^9$ is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, (a hydrogen atom and a hydroxy group) (a hydrogen atom and a hydrogen atom), or a group represented by the formula —$CH_2O$—;

Y is an oxo group, (a hydrogen atom and a hydroxy group) (a hydrogen atom and a hydrogen atom), or a group represented by the formula N—$NR^{11}R^{12}$ or N—$OR^{13}$;

each of $R^{11}$ and $R^{12}$ is independently a hydrogen atom, an alkyl group, an aryl group or a tosyl group;

each of $R^{13}$, $R^{14}$, $R^{15}$, $R^{16}$, $R^{17}$, $R^{18}$, $R^{19}$, $R^{22}$ and $R^{23}$ is independently a hydrogen atom or an alkyl group;

each of $R^{20}$ and $R^{21}$ is independently an oxo group or ($R^{20}$a and a hydrogen atom) or ($R^{21}$a and a hydrogen atom) in which each of $R^{20}$a and $R^{21}$a is independently a hydroxy group, an alkoxy group or a group represented by the formula —$OCH_2OCH_2CH_2OCH_3$, or $R^{21}$a is a protected hydroxy group, or $R^{20}$a and $R^{21}$a may together represent an oxygen atom in an epoxide ring;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkyl substituted by one or more hydroxy groups, an alkoxy, a benzyl and a group of the formula —$CH_2Se$ ($C_6H_5$)).

The above compound (I) or its pharmaceutically acceptable salt can be provided by the same technology as that described in the two patent gazettes referred to above. Particularly, the tricyclic compounds produced by fermenting *Streptomyces tsukubaensis* No. 9993 (FERM BP-927) or *Streptomyces hygroscopicus* subsp. *yakushimaensis* No. 7238 (FERM BP-928) are known by the identification nos. of FR-900506, FR-900520, FR-900523, and FR-900525 (Japanese Kokai Tokkyo Koho S61-148181).

The various definitions given in the above general formula (I), generic and subgeneric examples thereof, and preferred species are now explained and shown in detail.

The term "lower" means, unless otherwise indicated, a group having 1 to 6 carbon atoms.

Preferable examples of the "alkyl groups" include a straight or branched chain aliphatic hydrocarbon residue for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" are 1-(lower alkylthio) (lower) alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldimethylsilyl, propyldiphenylsilyl, tert-butyldiphenyl-silyl, etc.), more preferably tri($C_1$—$C_4$)alkylsilyl group and $C_1$–$C_4$ alkyl-diphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, arboxyhexanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-lower)alkylsilyl(lower)alkoxycarbonyl(lower)-alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy($C_1$–$C_4$)alkanoyl group having two ($C_1$–$C_4$) alkyls at the cycloalkyl moiety, camphorsulfonyl group, carboxy($C_1$–$C_4$)alkylcarbamoyl group, tri($C_1$–$C_4$) alkylsilyl($C_1$–$C_4$)alkoxycarbonyl($C_1$–$C_4$)alkylcarbamoyl group, benzoyl group optionally having one or two nitro groups, benzenesulfonyl group having halogen, orphenyl ($C_1$–$C_4$)alkanoyl group having $C_1$–$C_4$ alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

The pharmaceutically acceptable salt of the compound (I) includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the compound (I), it is to be understood that there may be conformers and one or more stereoisomers such as optical and geometrical isomers due to asymmetric carbon atom(s) or double bond(s), and such conformers and isomers are also included within the scope of the present invention.

The compound of the formula (I) or its pharmaceutically acceptable salt can be in the form of a solvate, which is included within the scope of the present invention. The solvate preferably include a hydrate and an ethanolate.

The preferred examples of the tricyclic compound (I) is the one, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

each of $R^{20}$ and $R^{21}$ is independently ($R^{20}$a and a hydrogen atom) or ($R^{21}$a and a hydrogen atom) in which each of $R^{20}$a and $R^{21}$a is a hydroxy group or an alkoxy group, or $R^{21}$a is a protected hydroxy group; and n is an integer of 1 or 2.

FK506 Substance is the most preferable compound belonging to the tricyclic compound (I). Other preferable compounds are listed hereinbelow.

1,14-Dihydroxy-12-[2-(4-hydroxy-3-methoxycyclohexyl)-1-methylvinyl]-23,25-dimethoxy-13,17,19,21,27-pentamethyl-11,28-dioxa-4-azatricyclo[(22.3.1.0$^{4,9}$]octacos-18-ene-2,3,10,16-tetraone, 12-[2-(4-acetoxy-3-methoxycyclohexyl)-1-methylvinyl]-17-allyl-1,14-dihydroxy-23,25-dimethoxy-13,19,21,27-tetramethyl-11,28-dioxa-4-azatricyclo[22.3.1.0$_{4,9}$]octacos-18-ene-2,3,10,16-tetraone, 17-allyl-1,14-dihydroxy-23,25-dimethoxy-13,19,21,27-tetramethyl-12-[2-[4-(3,5-dinitrobenzoyloxy)-3-methoxycyclo-hexyl]-1-methylvinyl]-11,28-dioxa-4-azatricyclo[22.3.1.0$^{4,9}$]-octacos-18-ene-2,3,10,16-tetraone, 17-allyl-12-[2-[4-[(−)-2-trifluoromethyl-2-methoxy-2-phenylacetoxy]-3-methoxycyclohexyl]-1-methylvinyl]-1,14-dihydroxy-23,25-dimethoxy-13,19,21,27-tetramethyl-11,28-dioxa-4-azatricyclo[22.3.1.0$_{4,9}$]octacos-18-ene-2,3,10,16-tetraone.

17-ethyl-1,14-dihydroxy-12-[2-(4-hydroxy-3-methoxycyclo-hexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR900520), and 17-ethyl-1,14,20-trihydroxy-12-[2-(3,4-dihydroxycyclo-hexyl)-1-methylvinyl]-23,25-dimethoxy-13,19,21,27-tetramethyl-11,28-dioxa-4-azatricyclo(22.3.1.0$_{4,9}$]octacos-18-ene-2,3,10,16-etraone.

The oil substance for use in this invention need only to be a substance capable of dissolving tricyclic compound (I) or its pharmaceutically acceptable salt. Preferable ones are, for example, fatty acid esters and alcohols.

Monohydric alcohol fatty acid esters (isopropyl myristate, ethyl myristate, butyl myristate, isocetyl myristate, octyldodecyl myristate, isopropyl palmitate, isostearyl palmitate, isopropyl isostearate, isocetyl isostearate, butyl stearate, isocetyl stearate, cetyl isooctanoate, ethyl linoleate, isopropyl linoleate, hexyl laurate, ethyl oleate, decyl oleate, oleyl oleate, octyl dodecyl myristate, hexyl decyl dimethyloctanoate, octyl dodecyl neodecanoate, etc.)

Dibasic acid diesters (diisopropyl adipate, dimethyl adipate, diethyl adipate, diisobutyl adipate, diethyl sebacate, diisopropyl sebacate, dipropyl sebacate, diethyl phthalate, diethyl pimelate, etc.)

Alcohols (oleyl alcohol, cetanol, stearyl alcohol, 2-octyldodecanol, etc.)

In this invention the above-mentioned oil substances can be used independently or in a combination of two or more species.

Particularly from the standpoint of stability of the dosage form, absorbability and/or irritation potential, it is preferable, in many instances, to use a plurality of such oil substances in combination. The preferred combination may for example be a mixture of a monohydric alcohol fatty acid ester (e.g. isopropyl myristate) and a dibasic acid diester (e.g. diethyl sebacate) in a suitable weight ratio (e.g. 0.1~10:1 (w/w), preferably 0.5~2:1 (w/w)). The most preferable weight ratio thereof is 1:1 (w/w).

The proportion of the oil substance in the pharmaceutical composition is preferably 2~50% (w/w), more preferably 10~40%, and most preferably 20~30%.

The surfactant for use in this invention is now described.

The surfactant that can be used includes pharmaceutically acceptable ionic or nonionic surfactants but is preferably a nonionic surfactant with an HLB number of not less than 10. More preferably, the following ether series and ester series surfactants can be mentioned.

Ethers

Polyoxyethylene alkyl ethers (polyoxyethylene oleyl ether, polyoxyethylene stearyl ether, polyoxyethylene cetyl ether, polyoxyethylene lauryl ether (Lauromacrogol J.P.), polyoxyethylene behenyl ether, etc.)

Esters

Polyoxyethylene sorbitan fatty acid esters Polyoxyethylene sorbitan monostearate, polyoxyethylene sorbitan monooleate, etc. (e.g. Tween 20, Tween 40, Tween 60, Tween 65, Tween 80, etc., all trademarks)

Polyethylene glycol fatty acid esters (polyethylene glycol monooleate, polyethylene glycol monostearate (e.g. polyoxyl stearate 40 J.P.), polyethylene glycol monolaurate, etc.)

Pentaglycerol fatty acid esters Pentaglycerol monolaurate, pentaglycerol monomyristate, pentaglycerol monooleate, pentaglycerol monostearate, etc.

Glycerol fatty acid esters Glyceryl monostearate etc.

In working this invention, the above-mentioned surfactants can be used independently or in a combination of two or more species. The proportion of the surfactant in the pharmaceutical composition is preferably 0.1~15% (w/w) and more preferably 0.5~5%(w/w).

The hydrophilic substance for use in this invention may be any substance that is pharmaceutically acceptable and capable of imparting viscosity to liquids, thus including the following organic or inorganic hydrophilic substances.

(1) Organic Substances

① Natural polymers . . . gum arabic, guar gum, carrageenin, gum tragacanth, pectin, starch, gum xanthan, gelatin, casein, dextrin, cellulose ② Semi-synthetic polymers . . . methylcellulose, ethylcellulose, hydroxyethylcellulose, hydroxypropylcellulose, carboxymethylcellulose sodium, carboxymethylcellulose calcium, carboxymethylstarch, sodium alginate, propylene glycol alginate, ③ Synthetic polymers . . . carboxyvinyl polymer (Carbopol) polyvinyl alcohol, polyvinylpyrrolidone, polyethylene glycol, polyvinyl methyl ether, sodium polyacrylate (2) Inorganic substances Bentonite, synthetic magnesium silicate, magnesium aluminosilicate, silicon oxide, etc.

The proportion of the hydrophilic substance in the pharmaceutical composition of this invention is selected according to the desired viscosity of the pharmaceutical composition and is preferably 0.1~10% (wlw) and more-preferably 0.5~2%.

Furthermore, in the instant invention, the pharmaceutical composition is preferably maintained at a constant pH from safety points of view. Therefore, a pH control agent such as a buffer, an aqueous solution of sodium hydroxide, or the like can be added in a suitable amount. The pH range is preferably 3.5~6 and more preferably 4~5.

Where necessary, in addition to the above ingredients, the conventional excipient (e.g. petrolatum, propylene glycol, etc.), stabilizer (antioxidant etc.), coloring agent, sweetener, flavor, diluent, antiseptic (e.g. parahydroxybenzoates, benzalkonium chloride, sorbic acid, etc.), and other drug substances effective against diseases of the skin can be added.

Meanwhile, the pharmaceutical composition of this invention can be produced by a process comprising the following steps.

(1) A step which comprises preparing a solution composed of said tricyclic compound (I) or pharmaceutically acceptable salt thereof, oil substance, and surfactant;

(2) a step which comprises mixing the solution with water to give an emulsion; and (3) a step which comprises mixing the emulsion with said hydrophilic substance, and further optionally pH control agent, with stirring. As an alternative, this step may comprise mixing said hydrophilic substance, and further optionally pH control agent, with water and, then, mixing the premix with the emulsion prepared as above with stirring.

The step (1) is preferably carried out at elevated temperature, for example at 50~90° C., preferably 60~80 ° C.

In step (2), the water for use is also preferably heated ahead of time to a temperature close to that of the solution prepared in step (1), and the resulting emulsion is preferably cooled to a suitable temperature, for example 30° C., before step (3) is carried out.

The dosage of tricyclic compound (I) or its pharmaceutically acceptable salt depends on the individual patient's age and the type and severity of disease but the usual daily therapeutic dose is about 0.001~1000 mg, preferably about 0.005~500 mg, and more preferably about 0.01~100 mg, as the active ingredient. Generally, an average of about 0.01 mg, 0.05 mg, 0.1 mg, 0.5 mg, 1 mg, 5 mg, 10 mg, 25 mg, or 50 mg per dose is administered.

The recommended proportion of tricyclic compound (I) in the pharmaceutical composition is 0.001~20% (w/w) preferably 0.01~10% (w/w), of the total composition.

EXAMPLES

The following examples illustrate the present invention in further detail, it being to be understood that those examples are not intended to limit the scope of the invention.

Example 1

The following ingredients (a), (b), and (c) were first admixed at 60~80° C. to prepare a solution, to which (d) previously warmed to 60~80° C. was added. The mixture was evenly emulsified with a homomixer and the resulting emulsion was cooled to 30° C. Then, (e) was added to the emulsion and the whole mixture was stirred to provide a pharmaceutical composition in the form of an easily spreadable cream [formulation (1)].

|  | Formulation (1) (% w/w) |
| --- | --- |
| (a) FK506 Substance | 0.1 |
| (b) Isopropyl myristate | 25.0 |
| (c) Polyoxyethylene [5.5] cetyl ether | 5.0 |
| (d) Purified water | 68.9 |
| (e) Carbopol 940 | 1.0 |

Example 2

A pharmaceutical composition (formulation (2)) was prepared according to a similar manner to that of Example 1, except that, after addition of (e), the mixture was adjusted to pH about 4.0 with a suitable amount of 1N-aqueous solution of NaOH (f).

Example 3

Pharmaceutical compositions (formulations (3) and (4)) were prepared according to a similar manner to that of Examples 1 and 2.

|  | Formulation (3) (% w/w) | Formulation (4) (% w/w) |
| --- | --- | --- |
| (a) FK506 Substance | 0.1 | 0.1 |
| (b) Isopropyl myristate | 25.0 | 25.0 |
| (c) Polyoxyethylene [7] cetyl ether | 5.0 | — |
| (c) Polyoxyethylene [10] oleyl ether | — | 5.0 |
| (d) Purified water | 68.9 | 68.9 |
| (e) Carbopol 940 | 1.0 | 1.0 |
| (f) 1N NaOH aq. sol. | q.s. | q.s. |

Example 4

Pharmaceutical compositions (formulations (5)–(8)) were prepared according to a similar manner to that of Examples 1 and 2.

| | | Formulation | | | |
|---|---|---|---|---|---|
| | | (5) (% w/w) | (6) (% w/w) | (7) (% w/w) | (8) (% w/w) |
| (a) | FK506 Substance | 0.1 | 0.1 | 0.1 | 0.1 |
| (b) | Isopropyl myristate | 25.0 | 25.0 | 25.0 | 25.0 |
| (c) | Pentaglycerol monolaurate | 5.0 | — | — | — |
| (c) | Pentaglycerol monomyristate | — | 5.0 | — | — |
| (c) | Pentaglycerol monooleate | — | — | 5.0 | — |
| (c) | Pentaglycerol monostearate | — | — | — | 5.0 |
| (d) | Purified water | 68.9 | 68.9 | 68.9 | 68.9 |
| (e) | Carbopol 940 | 1.0 | 1.0 | 1.0 | 1.0 |
| (f) | 1N-NaOH aq. sol. | q.s. | q.s. | q.s. | q.s. |

Example 5

Pharmaceutical compositions (formulations (9)–(12)) were prepared according to a similar manner to that of Examples 1 and 2.

| | | Formulation | | | |
|---|---|---|---|---|---|
| | | (9) (% w/w) | (10) (% w/w) | (11) (% w/w) | (12) (% w/w) |
| (a) | FK506 Substance | 0.1 | 0.1 | 0.1 | 0.1 |
| (b) | Isopropyl myristate | 25.0 | 25.0 | 25.0 | 25.0 |
| (c) | Glycerin monostearate | 5.0 | — | — | — |
| (c) | Polyethylene glycol monostearate | — | 5.0 | — | — |
| (c) | Polyoxyethylene-[20] sorbitan monostearate | — | — | 5.0 | — |
| (c) | Polyoxyethylene-[20] sorbitan monooleate | — | — | — | 5.0 |
| (d) | Purified water | 68.9 | 68.9 | 68.9 | 68.9 |
| (e) | Carbopol 940 | 1.0 | 1.0 | 1.0 | 1.0 |
| (f) | 1N-NaOH aq. sol. | q.s. | q.s. | q.s. | q.s. |

Example 6

Pharmaceutical compositions (formulations (13)–(16)) were prepared according to a similar manner to that of Examples 1 and 2.

| | | Formulation | | | |
|---|---|---|---|---|---|
| | | (13) (% w/w) | (14) (% w/w) | (15) (% w/w) | (16) (% w/w) |
| (a) | FK506 Substance | 0.1 | 0.1 | 0.1 | 0.1 |
| (b) | Diethyl sebacate | 25.0 | 25.0 | — | 25.0 |
| (b) | Oleyl alcohol | — | — | 25.0 | — |
| (c) | Polyoxyethylene-[10] behenyl ether | 5.0 | — | — | — |
| (c) | Polyoxyethylene-[5.5] cetyl ether | — | 5.0 | — | — |
| (c) | Polyoxyethylene-[21] lauryl ether | — | — | 5.0 | — |
| (c) | Polyoxyethylene [20] sorbitan monooleate | — | — | — | 5.0 |
| (d) | Purified water | 68.9 | 68.9 | 68.9 | 68.9 |
| (e) | Carbopol 940 | 1.0 | 1.0 | 1.0 | 1.0 |
| (f) | 1N-NaOH aq. sol. | q.s. | q.s. | q.s. | q.s. |

Example 7

The following ingredients (a), (b), and (c) were admixed at 60~80° C. to prepare a solution, to which ($d_1$) preheated to 60~80° C. was added. The mixture was evenly homogenized with a homomixer and, then, cooled to 30 ° C.

To this emulsion was added a gel prepared from (e) ($d_2$), and (f) and the mixture was stirred thoroughly to provide a pharmaceutical composition in the form of a well-spreadable cream [formulation (17)].

| | | Formulation (17) (% w/w) |
|---|---|---|
| (a) | FK506 Substance | 0.1 |
| (b) | Isopropyl myristate | 25.0 |
| (c) | Polyoxyethylene [5.5] cetyl ether | 5.0 |
| ($d_1$) | Purified water | 34.4 |
| (e) | Carbopol 940 | 1.0 |
| ($d_2$) | Purified water | 34.5 |
| (f) | 1N-NaO aq. sol. | q.s. |

Example 8

A pharmaceutical composition (formulation (18)) was prepared according to a similar manner to that of Example 7.

| | | Formulation (18) (% w/w) |
|---|---|---|
| (a) | FK506 Substance | 0.1 |
| (b) | Diethyl sebacate | 25.0 |
| (c) | Polyoxyethylene [20] sorbitan monooleate | 5.0 |
| ($d_1$) | Purified water | 34.4 |
| (e) | Carbopol 940 | 1.0 |
| ($d_2$) | Purified water | 34.5 |
| (f) | 1N-NaOH aq. sol. | q.s. |

Example 9

Pharmaceutical compositions (formulations (19)–(21)) were prepared according to a similar manner to that of Example 7.

|   |   | Formulation | | |
|---|---|---|---|---|
|   |   | (19) (% w/w) | (20) (% w/w) | (21) (% w/w) |
| (a) | FK506 Substance | 0.03 | 0.1 | 0.3 |
| ($b_1$) | Isopropyl myristate | 20 | 20 | 20 |
| ($b_2$) | Diethyl sebacate | 20 | 20 | 20 |
| (c) | polyoxyethylene [20] sorbitan monooleate | 2.5 | 2.5 | 2.5 |
| ($d_1$) + ($d_2$) | Purified water | 56.47 | 56.4 | 56.2 |
| (e) | Carbopol 940 | 1.0 | 1.0 | 1.0 |
| (f) | 1N-NaOH aq. sol. | q.s. | q.s. | q.s. |

Example 10

The protocol and results of a transdermal absorbability experiment using pharmaceutical compositions of the present invention are described below.

Transdermal Absorbability Test

Using the formulations 2, 3, 7, 12, and 20 prepared in the foregoing examples, an in vivo transdermal absorbability experiment was performed.

As experimental animals, 3 male 7-week-old SD rats were used. With the rat in supine position on a stereotactic apparatus, the hair coat in the abdominal region was clipped off with an electric clipper and, then, a depilatory cream (Eva-Cream, manufactured by Tokyo Tanabe Pharmaceutical) was applied. The skin area thus treated was washed with water 10 minutes after application of the cream for depilation. The rat was returned to its cage and allowed to rest for 24 hours. Thereafter, the rat was in supine position on the stereotactic apparatus, a rectangular area measuring 2.5 cm×4 cm was marked off at four corners on the depilated abdominal area of the rat and 50 mg of the test sample was applied over the square. At 1, 3, 5, 8, and 24 hours after this application, 0.3 ml of blood was drawn from the subclavian vein with an EDTA-pretreated syringe. After thorough mixing with EDTA, the blood was stored frozen until assayed.

Using the above blood samples, the whole blood FK506 Substance concentration was determined by enzyme-linked immunosorbent assay using peroxidase as the enzyme (e.g. shown in Japanese Kokai Tokkyo Koho H1-92659).

The transdermal absorption parameter was calculated for each test sample. The results are shown in Table 1. In Table 1, AUC [0–24 hr] represents the area under the blood concentration-time curve over 0–24 hours after application.

TABLE 1

Transdermal absorption parameter
(n = 3, mean ± S.E.)

| Test sample | AUC [0–24 hr] (ng.hr/ml) |
|---|---|
| Formulation 2 | >30 |
| Formulation 3 | >30 |
| Formulation 7 | >30 |
| Formulation 12 | >30 |
| Formulation 20 | >30 |

Effects of the Invention

In accordance with this invention there can be provided a pharmaceutical composition of tricyclic compound (I), particularly a hydrophilic semi-solid composition for external application, which is stable, easy to use, acceptable in feeling in use, and with a low irritation potential and/or improved dermal penetration.

The pharmaceutical composition of the present invention is useful for the treatment or prevention of Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata) because of the pharmacologic activities possessed by the tricyclic compound (I)

Furthermore, the active ingredient, tricyclic compound (I), used in the pharmaceutical composition is useful for the therapy or prophylaxis of the following diseases.

Rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

and infections caused by pathogenic microorganisms (e.g. Aspergillus fumigatus, Fusarium oxysporum, Trichophyton asteroides, etc.);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g. coeliac diseases, proctitis, eosinophilic gastroenteritis, mastocytosis, Crohn's disease and ulcerative colitis); food-related allergic diseases with symptomatic manifestation remote from the gastrointestinal tract (e.g. migrain, rhinitis and eczema);

renal diseases (e.g. intestitial nephritis, Goodpasture's syndrome, hemolytic uremic syndrome, and diabetic nephropathy); nervous diseases (e.g. multiple myositis, Guillain-Barre syndrome, Meniere's disease, multiple neuritis, solitary neuritis, cerebral infarction, Alzheimer's disease, Parkinson's disease, amyotrophiclateralsclerosis(ALS) and radiculopathy);

cerebral ischemic disease (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy)

endocrine diseases (e.g. hyperthyroidism, and Basedow's disease);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);

bone diseases (e.g. osteoporosis);

respiratory diseases (e.g. sarcoidosis, pulmonary fibrosis, and idiopathic interstitial pneumonia);

skin diseases (e.g. dermatomyositis, leukoderma vulgaris, ichthyosis vulgaris, photosensitivity, and cutaneous T-cell lymphoma);

circulatory diseases (e.g. arteriosclerosis, atherosclerosis, aortitis syndrome, polyarteritis nodosa, and myocardosis);

collagen diseases (e.g. scleroderma, Wegener's granuloma, and Sjogren's syndrome);

adiposis;

eosinophilic fasciitis;

periodontal diseases (e.g. damage to gingiva, periodontium, alveolar bone or substantia ossea dentis);

nephrotic syndrome (e.g. glomerulonephritis);

male pattern alopecia, alopecia senile;

muscular dystrophy;

pyoderma and Sezary syndrome;

Addison's disease;

chromosome abnormality-associated diseases (e.g. Down's syndrome);

active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.));

intestinal diseases (e.g. endotoxin shock, pseudomembranous colitis, and drug- or radiation-induced colitis): renal diseases (e.g. ischemic acute renal insufficiency, chronic renal failure);

pulmonary diseases (e.g toxicosis caused by pulmonary oxygen or drugs (e.g. paracort, bleomycin, etc.), lung cancer, and pulmonary emphysema);

ocular diseases (e.g. cataracta, iron-storage disease (siderosis bulbi), retinitis, pigmentosa, senile plaques, vitreous scarring, corneal alkali burn);

dermatitis (e.g. erythema multiforme, linear immunoglobulin A bullous dermatitis, cement dermatitis);

and other diseases (e.g. gingivitis, periodontitis, sepsis, pancreatitis, and diseases caused by environmental pollution (e.g. air pollution),aging, carcinogen, metastasis of carcinoma, and hypobaropathy)];

diseases caused by histamine release or leukotriene C4 release; restenosis of coronary artery following angioplasty and prevention of postsurgical adhesions;

Autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis);

Human Immunodeficiency Virus (HIV) infections AIDS; allergic conjunctivitis;

hypertrophic cicatrix or keloid due to trauma, burn, or surgery.

In addition, the tricyclic compound (I) has liver regenerating activity and/or activities of stimulating hypertrophy and hyperplasia of hepatocytes.

Therefore, the pharmaceutical composition of the present invention is useful for the therapy or prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

And further, the present composition is useful for preventing or treating various diseases because of its useful pharmacological activity such as augmenting activity of chemotherapeutic effect, activity of cytomegalovirus infection, anti-inflammatory activity, inhibiting activity against peptidyl-prolyl isomerase or rotamase, antimalarial activity, antitumor activity, and so on.

Among various formulations for the pharmaceutical composition of this invention, those formulations of reduced dermal irritancy are of value for treating or preventing atopic and other diseases of the skin, while those formulations with high dermal absorbability are particularly useful for treating or preventing psoriasis and other diseases of the skin.

What is claimed is:

1. A pharmaceutical composition, comprising:
   (A) a tricyclic compound of Formula (I) or a pharmaceutically acceptable salt of (A):

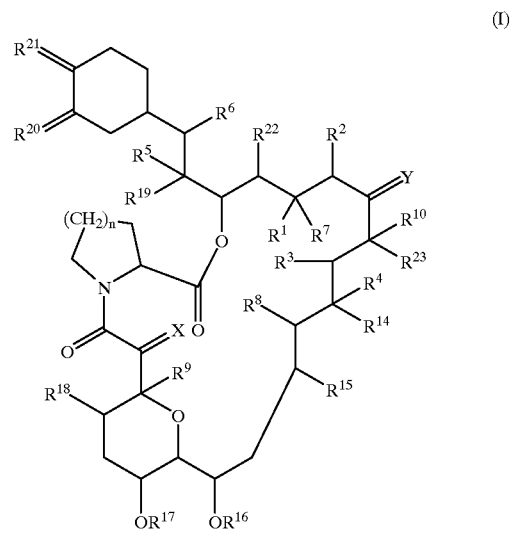

wherein
   each of adjacent pairs of $R^1$ and $R^2$, $R^3$ and $R^4$ or $R^5$ and $R^6$ independently
   (a) are two adjacent hydrogen atoms, or
   (b) may form another bond between the carbon atoms to which they are attached;
   $R^2$ is an alkyl group;
   $R^7$ is a hydrogen atom, a hydroxy group, a protected hydroxy group or alkoxy group, or an oxo group together with $R^1$;

each of $R^8$ and $R^9$ is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, (a hydrogen atom and a hydroxy group), two hydrogen atoms, or a group of formula -CH$_2$O-;

Y is an oxo group, (a hydrogen atom and a hydroxy group), two hydrogen atoms, or a group of formulas N—NR$^{11}$R$^{12}$ or N—OR$^{13}$;

each of $R^{11}$ and $R^{12}$ is independently a hydrogen atom, an alkyl group, an aryl group or a tosyl group;

each of $R^{13}$, $R^{14}$, $R^{15}$, $R^{16}$, $R^{17}$, $R^{18}$, $R^{19}$, $R^{22}$ and $R^{23}$ is independently a hyd or an alkyl group;

each of $R^{20}$ and $R^{21}$ is independently an oxo group, ($R^{20}$a and a hydrogen atom), or ($R^{21}$a and a hydrogen atom);

wherein each of $R^{20}$a and $R^{21}$a is independently a hydroxy group, an alkoxy group or a group of formula —OCH$_2$OCH$_2$CH$_2$OCH$_3$, or $R^{21}$a is a protected hydroxy group, or $R^{20}$a and $R^{21}$a both represent an oxygen atom in an epoxide ring;

n is an integer of 1 or 2; and

Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by at least one group selected from the group consisting of an alkyl, a hydroxy, an alkyl substituted by at least one hydroxy group, an alkoxy, a benzyl and a group of the formula —CH$_2$Se(C$_6$H$_5$);

(B) an oil substance combination of isopropyl myristate and diethyl sebacate;

(C) a surfactant which is selected from the group consisting of a polyoxyethylene alkyl ether, a polyoxyethylene sorbitan fatty acid ester, a pentaglycerol fatty acid ester and a glycerol fatty acid ester;

(D) a hydrophilic substance which is capable of imparting viscosity to liquids;

(E) water; and (F) optionally a pH control agent.

2. The pharmaceutical composition according to claim 1, wherein an amount of said surfactant, said oil substance and said hydrophilic substance is 0.1~15% by weight, 2~50% by weight, and 0.1~10% by weight, respectively, based on the total weight of said composition.

3. The pharmaceutical composition according to claim 1, wherein a pH of said pharmaceutical composition is 3.5~6.

4. The pharmaceutical composition according to claim 1, wherein said hydrophilic substance is a carboxyvinyl polymer.

5. The pharmaceutical composition according to claim 1, wherein said surfactant is a polyoxyethylene sorbitan fatty acid ester.

6. The pharmaceutical composition according to claim 1, wherein in said tricyclic compound of Formula (I) each of said adjacent pairs of $R^3$ and $R^4$ or $R^5$ and $R^6$ independently may form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is a hydrogen atom and a hydrogen atom or an oxo group;

Y is an oxo group;

each of $R^4$, $R^{15}$, $R^{16}$, $R^{17}$, $R^{18}$, $R^{19}$, and $R^{22}$ is a methyl group;

each of $R^{20}$ and $R^{21}$ is independently ($R^{20}$a and a hydrogen atom) or ($R^{21}$a and a hydrogen atom);

wherein each of $R^{20}$a and $R^{21}$a is a hydroxy group or an alkoxy group, or $R^{21}$a is a protected hydroxy group; and n is an integer of 1 or 2.

7. The pharmaceutical composition according to claim 6, wherein said tricyclic compound of Formula (I) is 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

8. The pharmaceutical composition according to claim 7, wherein a pH of said pharmaceutical composition is about 4-5.

9. A process for producing the pharmaceutical composition claimed in claim 1, comprising:

mixing a solution comprising said tricyclic compound of Formula (I) or said pharmaceutically acceptable salt of (A), said oil substance and said surfactant with water to prepare an emulsion; and mixing said emulsion with said hydrophilic substance and optionally said pH control agent.

10. The process according to claim 9, comprising:

separately mixing said hydrophilic substance and optionally said pH control agent with water, thereby providing a mixture; and mixing said mixture with said emulsion.

* * * * *

UNITED STATES PATENT AND TRADEMARK OFFICE
CERTIFICATE OF CORRECTION

PATENT NO. : 6,387,918 B1
DATED : May 14, 2002
INVENTOR(S) : Masayuki Yamanaka et al.

It is certified that error appears in the above-identified patent and that said Letters Patent is hereby corrected as shown below:

Column 1,
Line 20, "S61-1481B1," should read -- S61-148181, --;
Line 33, "*vakushimaensis*" should read -- *yakushimaensis* --.

Column 2,
Line 9, "However no" should read -- However, no --.

Column 4,
Line 11, "ethyldimethylsilyl," should read -- ethyldiphenylsilyl, --;
Line 24, "arboxylhexanoyl," should read -- carboxyhexanoyl, --.

Column 5,
Line 1, "orphenyl" should read -- or phenyl --;
Line 54, "4-azatricyclo[(22.3.1.0$^{4,9}$]octacos-18-ene-2,3,10,16-" should read
-- 4-azatricyclo[22.3.1.0$^{4,9}$]octacos-18-ene-2,3,10,16- --;
Line 58, "[22.3.1.0$_{4,9}$]" should read -- [22.3.1.0$^{4,9}$] --.

Column 6,
Lines 2-3, "[22.3.1.0$_{4,9}$]" should read -- [22.3.1.0$^{4,9}$] --;
Line 10, "-methylvinyl-" should read -- -methylvinyl]- --.
Line 11, "4-azatricyclo[(22.3.1.0$_{4,9}$]" should read -- 4-azatricyclo[22.3.1.0$^{4,9}$] --;
Line 12, "etraone." should read -- tetraone. --.

Column 7,
Line 32, "(wIw)" should read -- (w/w) --.

Column 8,
Line 12, "(w/w)" should read -- (w/w), --.

Column 10,
Line 27, "(e)(d$_2$)," should read -- (e), (d$_2$), --.

UNITED STATES PATENT AND TRADEMARK OFFICE
CERTIFICATE OF CORRECTION

PATENT NO. : 6,387,918 B1
DATED : May 14, 2002
INVENTOR(S) : Masayuki Yamanaka et al.

It is certified that error appears in the above-identified patent and that said Letters Patent is hereby corrected as shown below:

<u>Column 12,</u>
Line 64, "amyotrophiclateralsclerosis(ALS)" should read -- amyotrophic lateral sclerosis (ALS) --.

<u>Column 13,</u>
Line 2, "encephalopathy)" should read -- encephalopathy); --;
Line 54, "pollution),aging" should read -- pollution), aging --.

<u>Column 15,</u>
Line 18, "hyd" should read -- hydrogen atom --.

<u>Column 16,</u>
Line 20, "$R^4$," should read -- $R^{14}$, --.

Signed and Sealed this

Seventeenth Day of June, 2003

JAMES E. ROGAN
*Director of the United States Patent and Trademark Office*